(12) United States Patent
Galli et al.

(10) Patent No.: US 7,585,974 B2
(45) Date of Patent: *Sep. 8, 2009

(54) DERIVATIVES OF 5-(PYRIDIN-3-YL)-1-AZABICYCLO[3.2.1]OCTANE, THEIR PREPARATION AND THEIR THERAPEUTIC APPLICATION

(75) Inventors: Frederic Galli, Vaucresson (FR); Odile LeClerc, Massy (FR); Alistair Lochead, Charenton le Pont (FR); Alain Nedelec, Paris (FR)

(73) Assignee: Sanofi-Aventis, Paris (FR)

( * ) Notice: Subject to any disclaimer, the term of this patent is extended or adjusted under 35 U.S.C. 154(b) by 100 days.

This patent is subject to a terminal disclaimer.

(21) Appl. No.: 11/696,993

(22) Filed: Apr. 5, 2007

(65) Prior Publication Data

US 2007/0185137 A1    Aug. 9, 2007

Related U.S. Application Data

(63) Continuation of application No. 10/500,015, filed as application No. PCT/FR03/00004 on Jan. 3, 2003, now Pat. No. 7,223,750.

(30) Foreign Application Priority Data

Jan. 7, 2002    (FR) .................... 02 00109

(51) Int. Cl.
  *C07D 237/00* (2006.01)
  *C07D 401/00* (2006.01)
  *C07D 221/99* (2006.01)
(52) U.S. Cl. .................. 544/240; 544/310; 546/112
(58) Field of Classification Search ................ 546/112; 544/240, 310
See application file for complete search history.

(56) References Cited

U.S. PATENT DOCUMENTS 5,817,679 A    10/1998    Shen et al.
6,407,095 B1    6/2002    Lochead et al.
6,635,645 B1    10/2003    Lochead et al.
7,223,750 B2 *    5/2007    Galli et al. ............. 514/217.03

FOREIGN PATENT DOCUMENTS

WO    WO 95/03306    2/1995

OTHER PUBLICATIONS

Mihailescu, S., et al., Nicotine, Brain Nicotinic Receptors, and Neuropsychiatric Disorders, Archive of Medical Research vol. 31, (2000) pp. 131-144.
Mihailescu, S., et al., Nicotine and Brain Disorders, PMID: 11263271 (2000).

* cited by examiner

*Primary Examiner*—Janet L Andres
*Assistant Examiner*—Binta M Robinson
(74) *Attorney, Agent, or Firm*—Balaram Gupta

(57) ABSTRACT

Compounds complying with the general formula

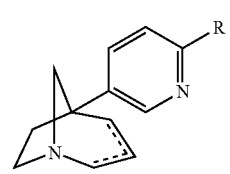

(I)

in which R either represents a halogen atom or a phenyl group substituted by one or more groups chosen from halogen atoms and $(C_1-C_6)$alkyl, $(C_1-C_6)$alkoxy, nitro, amino, trifluoromethyl, cyano, hydroxy, acetyl or methylenedioxy groups, or represents a pyridinyl group, a thienyl group, an indolyl group, or a pyrimidinyl group optionally substituted by one or more $(C_1-C_6)$alkoxy groups, where, of the two carbon-carbon bonds represented by ⹀, one is single and the other may be single or double. The compounds of this invention are useful as therapeutic agents.

2 Claims, No Drawings

DERIVATIVES OF 5-(PYRIDIN-3-YL)-1-AZABICYCLO[3.2.1]OCTANE, THEIR PREPARATION AND THEIR THERAPEUTIC APPLICATION

CROSS REFERENCE TO RELATED APPLICATIONS

This application is a continuation of U.S. application Ser. No. 10/500,015, filed Jun. 23, 2004, now allowed, which was the National Stage of International application No. PCT/FR03/00,004, filed Jan. 3, 2003, both of which are incorporated herein by reference in their entireties; which claims the benefit of priority of French Patent Application No. 02/00, 109, filed Jan. 7, 2002.

The present invention relates to compounds which are ligands for nicotinic receptors and which are useful in the treatment or the prevention of disorders linked to a dysfunction of nicotinic receptors, in particular at the central nervous system level.

The compounds of the present invention comply with the general formula (I)

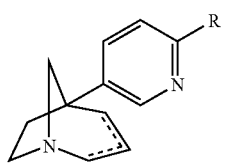

(I)

in which R represents a halogen atom or a ($C_3$-$C_6$)cycloalkyl group or a phenyl group substituted by one or more groups chosen from a halogen atom, or a ($C_1$-$C_6$)alkyl, ($C_1$-$C_6$) alkoxy, nitro, amino, ($C_1$-$C_3$) dialkylamino, trifluoromethyl, trifluoromethoxy, cyano, hydroxy, acetyl or methylenedioxy group, or a piperidinyl, or morpholin-4-yl, or pyrrolidin-1-yl, or azetidin-1-yl, or azepin-1-yl, or pyridinyl, or quinolinyl, or thienyl, or pyrazinyl, or furyl, or benzofuryl, or benzothienyl, or indolyl, or pyrimidinyl, or isoxazolyl, or phenoxazinyl, or phenoxathiinyl, or dibenzothienyl, or dibenzofuryl, or pyrrolyl, or naphthyl group, where each of these groups may optionally be substituted by one or more groups chosen from halogen atoms, ($C_1$-$C_6$)alkyl, ($C_1$-$C_6$)alkoxy, trifluoromethoxy, trifluoromethyl, nitro, cyano, hydroxy, amino, ($C_1$-$C_3$)dialkylamino or ($C_3$-$C_8$) cycloalkylamino groups.

Of the two carbon-carbon bonds represented by ----; one is single and the other may be single or double. Furthermore, the carbon atom in position 5 is asymmetric, and therefore the compounds may exist in the form of two enantiomers or of mixtures of these latter.

The compounds of the invention may exist in the form of bases or of salts derived from addition to acids.

A subset of preferred compounds is that of the compounds of general formula (I) in which R either represents a halogen atom or a phenyl group substituted by one or more groups chosen from halogen atoms and ($C_1$-$C_6$)alkyl, ($C_1$-$C_6$)alkoxy, nitro, amino, trifluoromethyl, cyano, hydroxy, acetyl or methylenedioxy groups, or represents a pyridinyl group, or a thienyl group, or an indolyl group, or a pyrimidinyl group optionally substituted by one or more ($C_1$-$C_6$) alkoxy groups.

The compounds of the general formula (I) may be prepared by a process illustrated by the following scheme. 3-Oxo-1,4-azabicyclo[2.2.2]octane, of formula (II), is reacted with a pyridine derivative of general formula (III), in which R is as defined above and W represents a halogen atom.

It is also possible to carry out a condensation reaction between 3-oxo-1-azabicyclo[2.2.2]octane and the lithiated derivative of the compounds of general formula (III) obtained by halogen-metal exchange with an alkyl lithium derivative.

This gives compounds of general formula (IV) which, when treated with heat in an acid medium lead to compounds of the general formula (I) in which one of the two carbon-carbon bonds represented by ----, is double. Catalytic hydrogenation of the double bond leads to compounds of general formula (I) in which all the bonds of the azabicyclooctane ring are saturated.

3-Oxo-1-azabicyclo[2.2.2]octane is commercially available.

The compounds of general formula (III) are commercially available or are accessible by methods described in the literature.

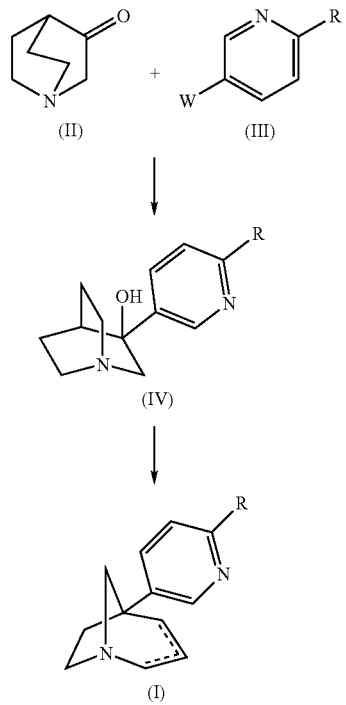

Scheme

For certain compounds, the substituents R are not present in the starting compound of general formula (III); depending on their nature, these substituents may be introduced on the final compound of general formula (I). Thus, for example, compounds of general formula (I) in which R represents an aryl group may be prepared starting from corresponding compounds in whose formula R represents a halogen atom, using any of the known methods, such as Suzuki coupling in the presence of a boronic acid and of a palladium catalyst, e.g. tetrakis(triphenylphosphine)palladium, or Stille coupling with the appropriate reactants.

The following examples illustrate the preparation of some compounds of the invention.

Elemental microanalyses and IR and NMR spectra confirm the structures of the compounds obtained.

The numbers indicated in brackets in the titles of the examples correspond to those in the first column of the table below.

In the names of the compounds, the hyphen "-" is part of the word, whereas the underscore "_" serves merely as the break at the end of a line, and is to be deleted in the absence of a break, and must not be replaced by a standard hyphen or by a space.

EXAMPLE 1

Compound No. 1

Hydrobromide of 5-(2-phenylpyridin-5-yl)-1-azabicyclo[3.2.1]oct-3-ene (2:1)

1.1. 5-Bromo-2-phenylpyridine 30 g (0.127 mol) of 2,5-dibromopyridine in suspension in 100 ml of toluene, 15.4 g (0.127 mol) of phenylboronic acid, 4.4 g (0.0038 mol) of tetrakis(triphenylphosphine)palladium, 90 ml of a 2M aqueous solution of sodium carbonate and 4 ml of ethanol are introduced in succession into a 500 ml three-necked flask, and the mixture is heated at 90° C. for 22 h.

The mixture is decanted, the organic phase is washed with 100 ml of water and dried and concentrated under reduced pressure, and the residue is purified by chromatography on a silica gel column, eluting with a 30/70 mixture of cyclohexane and dichloromethane.

This gives 22.4 g of crystals.

Melting point: 69-72° C.

1.2. 3-Hydroxy-3-(2-phenylpyridin-5-yl)-1-azabicyclo[2.2.2]octane 2.5 g (0.0107 mol) of 5-bromo-2-phenylpyridine in solution in 40 ml of ethyl ether are introduced into a 100 ml three-necked flask, and the reaction mixture is cooled to −60° C. before dropwise addition during 10 minutes of 5.6 ml (0.0139 mol) of a 2.5 M solution of n-butyllithium in hexane, and the temperature is held at −70° C. for 1 h.

1.34 g (0.0107 mol) of 1-azabicyclo[2.2.2]octan-3-one in solution in 20 ml of tetrahydrofuran is added during 10 min, and the mixture is stirred for 30 min at −70° C. then at ambient temperature for 4 h.

The reaction mixture is hydrolyzed by adding 100 ml of methanol and is concentrated under reduced pressure.

The residue is taken up in 100 ml of a saturated aqueous solution of ammonium chloride and the aqueous phase is extracted with chloroform. The organic phases are dried and concentrated under reduced pressure and the residue is purified by chromatography on a silica gel column, eluting with a 90/10/1 mixture of chloroform, methanol and ammonia. This gives 0.8 g of crystals.

Melting point: 214° C.

1.3. Hydrobromide of 5-(2-phenylpyridin-5-yl)-1-azabicyclo[3.2.1]oct-3-ene (2:1)

0.8 g (2.85 mmol) of 3-hydroxy-3-(2-phenylpyridin-5-yl)-1-azabicyclo[2.2.2]octane and then 10 ml of methanesulfonic acid are introduced into a 25 ml three-necked flask and the mixture is heated to 180° C. for 24 h.

The mixture is poured onto ice and rendered alkaline by adding a concentrated aqueous solution of sodium hydroxide, the aqueous phase is extracted with chloroform, and the organic phase is dried and concentrated under reduced pressure. The residue is purified by chromatography on a silica gel column, eluting with a 98/2/0.2 mixture of chloroform, methanol and ammonia.

This gives 0.25 g of product, the dihydrobromide of which is made by adding a 5.7 M solution of hydrobromic acid in acetic acid.

This gives 0.22 g of dihydrobromide.

Melting point: 273-274° C.

EXAMPLE 2

Compound No. 2

Hydrobromide of 5-(2-phenylpyridin-5-yl)-1-azabicyclo[3.2.1]octane (2:1)

0.14 g (0.33 mmol) of dihydrobromide of 5-(2-phenylpyridin-5-yl)-1-azabicyclo[3.2.1]oct-3-ene in solution in 20 ml of methanol are introduced into a 250 ml Parr bottle, and 0.14 g of palladium, 10% adsorbed on carbon, is added. The reaction mixture is then submitted to a pressure of 0.35 MPa of hydrogen, with stirring, for 5 h.

The catalyst is recovered via filtration through diatomaceous earth and the solvent is concentrated under reduced pressure.

This gives 0.058 g of product.

Melting point: 272-277° C.

EXAMPLE 3

Compound No. 8

Ethanedioate of 5-[2-(3-methylphenyl)pyridin-5-yl)-1-azabicyclo[3.2.1]oct-3-ene (1:1)

3.1. 3-Hydroxy-3-(2-bromopyridin-5-yl)-1-azabicyclo[2.2.2]octane 27.6 g (0.116 mol) of 2,5-dibromopyridine in 1 000 ml of ethyl ether are introduced into a 2 000 ml three-necked flask, the reaction mixture is cooled to −67° C. and 56 ml (0.140 mol) of a 2.5 M solution of butyllithium in hexane are added dropwise in 10 min.

The mixture is stirred at −67° C. for 45 min before adding 14.5 g (0.116 mol) of 1-azabicyclo[2.2.2]octan-3-one in solution in 150 ml of ethyl ether in 45 min, and the mixture is stirred at −67° C. for 3 h.

300 ml of a saturated aqueous solution of ammonium chloride are added followed by 200 ml of a concentrated aqueous solution of sodium hydroxide, the aqueous phase is extracted with chloroform, and the organic phases are dried and concentrated under reduced pressure. The residue is purified by chromatography on a silica gel column, eluting with a 95/5/0.5, then 80/15/1.5, mixture of chloroform, methanol and ammonia.

This gives 19.7 g of product in the form of amorphous solid.

3.2. 5-(2-bromopyridin-5-yl)-1-azabicyclo[3.2.1]oct-3-ene 9.4 g (0.033 mol) of 3-hydroxy-3-(2-bromopyridin-5-yl)-1-azabicyclo[2.2.2]octane and 35 ml of concentrated sulfuric acid are introduced into a 100 ml three-necked flask and the mixture is heated at 190° C. for 1 h 45.

The mixture is cooled and poured onto 400 ml of an ice-cold aqueous sodium hydroxide solution, the aqueous phase is extracted with chloroform, and the organic phases are dried and evaporated under reduced pressure.

The residue is purified by chromatography on a silica gel column, eluting with a 90/10/1 mixture of chloroform, methanol and ammonia.

This gives 3.9 g of product in the form of a pale yellow solid.

Melting point: 73-75° C.

3.3. Ethanedioate of 5-[2-(3-methylphenyl)pyridin-5-yl)-1-azabicyclo[3.2.1]oct-3-ene (1:1)

0.2 g (0.75 mmol) of 5-(2-bromopyridin-5-yl)-1-azabicyclo[3.2.1]oct-3-ene, 3 ml of toluene, 0.7 ml of a 2 M aqueous solution of sodium carbonate, 0.147 g (1.05 mmol) of 3-methylbenzeneboronic acid, 0.042 g (0.04 mmol) of tetrakis(triphenylphosphino)palladium and 0.7 ml of ethanol are introduced in succession into a 10 ml tube and the mixture is heated at 100° C. for 15 h.

The aqueous phase is removed by decanting and the crude product is extracted on a DOWEX® (ion exchange resin) resin column by washing in succession with methanol and then chloroform before eluting with a solution of ammonia. The residue is purified by chromatography on a silica gel column, eluting with a 90/10/1 mixture of chloroform, methanol and ammonia. This gives 0.167 g of product in the form of oil, which is dissolved in 2 ml of isopropyl alcohol to form an ethanedioate by adding 0.051 g (0.057 mmol) of ethanedioic acid in solution in isopropyl alcohol. This gives 0.188 g of crystallized product.

Mp: 173-174° C.

EXAMPLE 4

Compound No. 26

Hydrobromide of 5-[2-(3-fluorophenyl)pyridin-5-yl)-1-azabicyclo[3.2.1]octane 2:1

0.18 g (0.51 mmol) of the ethanedioate of 5-[2-(3-fluorophenyl)pyridin-5-yl)-1-azabicyclo[3.2.1]oct-3-ene in solution in 20 ml of methanol are introduced into a 250 ml Parr bottle, and 0.36 g of palladium, 10% adsorbed on carbon, is added, and the reaction mixture is submitted to a pressure of 0.42 MPa of hydrogen, with stirring, at 45° C. for 6 h.

The catalyst is recovered by filtration on diatomaceous earth, the filtrate is concentrated under reduced pressure, the residue is taken up in 10 ml of an N aqueous solution of sodium hydroxide, and the aqueous phase is extracted with chloroform, and the crude product is purified by chromatography on a silica gel column, eluting with a 80/20/2 mixture of chloroform, methanol and ammonia. This gives 0.085 g of product, the dihydrobromide of which is made by adding 0.107 ml of a 33% solution of hydrobromic acid in acetic acid. This gives 0.097 g of crystals.

Melting point: 98-100° C.

The table which follows illustrates the chemical structures and the physical properties of some compounds of the invention. In the column "R", "(+)" indicates the dextrorotatory enantiomer and "(−)" the laevorotatory enantiomer; the compounds not annotated in that column are racemates. In the "=" column, the number indicated corresponds to the position of the double bond in the case of a 1-azabicyclooctene, and "−" indicates a saturated heterocycle. In the "salt" column, "−" indicates a compound in the form of a base, "HBr" indicates a hydrobromide and "ox." indicates an oxalate. The corresponding molar acid:base ratios are indicated. In the column "M(° C.)", "(d)" indicates a melting point with decomposition.

TABLE

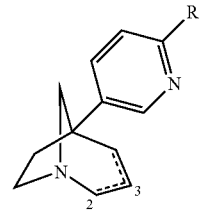

(I)

| No. | R | = | Salt | M(° C.) |
|---|---|---|---|---|
| 1 | $C_6H_5$ | 3 | HBr 2:1 | 273-274 |
| 2 | $C_6H_5$ | — | HBr 2:1 | 272-277 |
| 3 | $C_6H_5$ | 2 | HBr 2:1 | 297-305 |
| 4 | 2,4-$(OCH_3)_2$-5-pyrimidinyl | 2 | HBr 2:1 | 340 (d) |
| 5 | 3,4-$(OCH_3)_2$-$C_6H_3$ | 3 | HBr 2:1 | 261-262 |
| 6 | 3,4-$(OCH_3)_2$-$C_6H_3$ | — | HBr 2:1 | 234-236 |
| 7 | 2-F—$C_6H_4$ | 3 | ox. 1:1 | 157-158 |
| 8 | 3-$CH_3$—$C_6H_4$ | 3 | ox. 1:1 | 173-174 |
| 9 | 3-F—$C_6H_4$ | 3 | ox. 1:1 | 163-164 |
| 10 | 3-$NO_2$—$C_6H_4$ | 3 | ox. 1:1 | 183-184 |
| 11 | 3-$CF_3$—$C_6H_4$ | 3 | ox. 1:1 | 156-157 |
| 12 | 4-$CH_3$—$C_6H_4$ | 3 | ox. 1:1 | 213-215 |
| 13 | 3-Thienyl | 3 | ox. 1:1 | 189-190 |
| 14 | 3,4-$OCH_2O$—$C_6H_3$ | 3 | ox. 1:1 | 201-202 |
| 15 | 4-Cl—$C_6H_4$ | 3 | ox. 1:1 | 201-203 |
| 16 | 3-$CH_3CO$—$C_6H_4$ | 3 | ox. 1:1 | 155-156 |
| 17 | 3-Pyridinyl | 3 | ox. 1:1 | 183-184 |
| 18 | 5-Indolyl | 3 | ox. 1:1 | 253-254 |
| 19 | 4-$CH_3O$—$C_6H_4$ | 3 | ox. 1:1 | 205-207 |
| 20 | 3,5-$(CH_3)_2$—$C_6H_3$ | 3 | ox. 1:1 | 192-193 |
| 21 | 4-Pyridinyl | 3 | ox. 1:1 | 172-174 |
| 22 | 4-$CH_3O$—$C_6H_4$ | — | HBr 2:1 | 246-247 |
| 23 | 4-$CH_3$—$C_6H_4$ | — | HBr 2:1 | 295-297 |
| 24 | 3-$CH_3$—$C_6H_4$ | — | HBr 2:1 | 284-287 |
| 25 | 3,5-$(CH_3)_2$—$C_6H_3$ | — | HBr 2:1 | 250-254 |
| 26 | 3-F—$C_6H_4$ | — | HBr 2:1 | 98-100 |
| 27 | 3-Thienyl | — | HBr 2:1 | 193-196 |
| 28 | 3,4-$OCH_2O$—$C_6H_3$ | — | HBr 2:1 | 260-263 |
| 29 | 2-F—$C_6H_4$ | — | HBr 2:1 | 266-269 |
| 30 | 3-Pyridinyl | — | HBr 3:1 | 256-260 |
| 31 | 4-Pyridinyl | — | HBr 2:1 | 249-253 |
| 32 | 3-$NO_2$—$C_6H_4$ | — | HBr 3:1 | 264-267 |
| 33 | 3-$CF_3$—$C_6H_4$ | — | HBr 2:1 | 218-221 |
| 34 | Br | 3 | HBr 2:1 | 234-236 |
| 35 | Br | 2 | HBr 2:1 | >350 |
| 36 | 4-Piperidinyl | — | HBr 3:1 | 289-292 |
| 37 | 3-Piperidinyl | — | HBr 3:1 | 261-265 |
| 38 | 4-$CH_3O$—$C_6H_4$ (+) | — | — | 125-129 |
| 39 | 4-$CH_3O$—$C_6H_4$ (−) | — | — | 125-129 |
| 40 | 3-F—$C_6H_4$ (+) | — | — | 68-70 |
| 41 | 3-F—$C_6H_4$ (−) | — | — | 68-70 |
| 42 | 2-Thienyl | — | HBr 2:1 | 251 (d) |
| 43 | 2-Thienyl | 3 | HBr 2:1 | 246-247 |

TABLE-continued (I)

[Structure: bicyclic amine (position 2,3) connected to pyridine bearing substituent R]

| No. | R | = | Salt | M(° C.) |
|---|---|---|---|---|
| 44 | 5-CH₃-2-thienyl | 3 | HBr 2:1 | 237-238 |
| 45 | 5-CH₃-2-thienyl | — | HBr 2:1 | 210-211 |
| 46 | 5-Cl-2-thienyl | — | HBr 2:1 | 248-250 |
| 47 | 5-Cl-2-thienyl | 3 | HBr 2:1 | 258-259 |
| 48 | 2-Furyl | 3 | HBr 2:1 | 262-264 |
| 49 | 2-Furyl | — | HBr 2:1 | 182 (d) |
| 50 | 5-Indolyl | — | ox. 1:1 | 268-269 |
| 51 | 2-Benzofuryl | 3 | — | 145-146 |
| 52 | 2-Benzofuryl | — | HBr 2:1 | 303-305 |
| 53 | 2-Pyrrolyl | 3 | HBr 2:1 | 265-266 |
| 54 | 2-Pyrrolyl | — | ox. 1:1 | 95-97 |
| 55 | 2-Benzothienyl | 3 | — | 165-166 |
| 56 | 2-Benzothienyl | — | HBr 2:1 | 311-313 |
| 57 | 3-Furyl | 3 | HBr 2:1 | 291-294 |
| 58 | 3-Furyl | — | HBr 2:1 | 313-315 |
| 59 | 4-OH-3-pyridinyl | — | HBr 2:1 | 268-270 |
| 60 | 3,5-(CH₃)₂-1,2-oxazol-4-yl | — | — | 116-117 |
| 61 | 3,5-(CH₃)₂-1,2-oxazol-4-yl | 3 | HBr 2:1 | 250-252 |
| 62 | 2,4-(CH₃O)₂-pyrimidin-5-yl | — | ox. 1:1 | 70-72 |
| 63 | 4-CH₃-2-thienyl | — | HBr 2:1 | 336-338 |
| 64 | 4-CH₃-2-thienyl | 3 | HBr 2:1 | 284-285 |
| 65 | 1-Dibenzofuryl | — | HBr 2:1 | 188-189 |
| 66 | 1-Dibenzofuryl | 3 | HBr 2:1 | 302-304 |
| 67 | 1-Phenoxathiinyl | 3 | HBr 2:1 | 292-293 |
| 68 | 1-Phenoxathiinyl | — | HBr 1:1 | 200-203 |
| 69 | 8-Quinoleinyl | — | HBr 2:1 | 206-208 |
| 70 | 8-Quinoleinyl | 3 | HBr 2:1 | 309-310 |
| 71 | 3-Benzothienyl | 3 | HBr 2:1 | 222-223 |
| 72 | 3-Benzothienyl | — | ox. 1:1 | 80-82 |

The compounds of the present invention have been studied for their affinity in relation to nicotinic receptors containing the $\alpha_4\beta_2$ subunit, using the methods described by Anderson and Arneric in *Eur. J. Pharmacol.* (1994), 253, 261 and by Hall et al. in *Brain Res.* (1993), 600, 127. Male Sprague Dawley rats weighing from 150 to 200 g are decapitated and the entire brain is rapidly removed, homogenized in 15 volumes of a 0.32 M sucrose solution at 4° C. and then centrifuged at 1 000 g for 10 min. The pellet is removed and the supernatant is centrifuged at 20 000 g for 20 min at 4° C. The pellet is recovered and homogenized with the aid of a Polytron™ mill in 15 volumes of doubly-distilled water at 4° C., then centrifuged at 8 000 g for 20 min. The pellet is removed and the supernatant and the skin layer (buffy coat) are centrifuged at 40 000 g for 20 min, and the pellet is recovered and suspended in 15 ml of doubly-distilled water and centrifuged again at 40 000 g prior to storage at −80° C. On the day of the experiment, the tissue is slowly defrosted and is suspended in 3 volumes of buffer. 150 μl of this membrane suspension are incubated at 4° C. for 120 min in the presence of 100 μl of 1 nM [³H]-cytisine in a final volume of 500 μl of buffer, in the presence or absence of test compound.

The reaction is halted by filtration through Whatman GF/B™ filters pretreated with polyethyleneimine, the filters are rinsed twice, each time with 5 ml of buffer at 4° C., and the radioactivity retained on the filter is measured by liquid scintigraphy. The nonspecific binding in the presence of 10 μM (−)-nicotine is determined; the nonspecific binding represents from 75 to 85% of the total binding recovered on the filter.

For each concentration of compound studied, the percentage of inhibition of the specific binding of [³H]-cytisine is determined, and then the $IC_{50}$ value, the concentration of compound which inhibits 50% of the specific binding, is calculated.

The $IC_{50}$ values for the highest-affinity compounds of the invention are from 0.01 to 10 μM.

The compounds of the invention were also studied for their affinity in relation to nicotinic receptors containing the $\alpha_7$ subunit, using the methods described by Mark and Collins in *J. Pharmacol. Exp. Ther.* (1982), 22, 564 and by Marks et al. in *Mol. Pharmacol.* (1986), 30, 427.

Male OFA rats weighing from 150 to 200 g are decapitated and the entire brain is rapidly removed, homogenized in 15 volumes of a 0.32 M sucrose solution at 4° C. and then centrifuged at 1 000 g for 10 min. The pellet is removed and the supernatant is centrifuged at 8 000 g for 20 min at 4° C. The pellet is recovered and homogenized with the aid of a Polytron™ mill in 15 volumes of doubly-distilled water at 4° C., then centrifuged at 8 000 g for 20 min. The pellet is removed and the supernatant and the skin layer (buffy coat) are centrifuged at 40 000 g for 20 min, and the pellet is recovered and suspended in 15 ml of doubly-distilled water and centrifuged again at 40 000 g prior to storage at −80° C. On the day of the experiment, the tissue is slowly defrosted and is suspended in 5 volumes of buffer. 150 μl of this membrane suspension are preincubated at 37° C. for 30 min in darkness in the presence or absence of the test compound. The membranes are then incubated for 60 min at 37° C. in darkness in the presence of 50 μl of 1 nM [³H]α-bungarotoxin in a final volume of 250 μl of 20 mM HEPES buffer, 0.05% polyethyleneimine. The reaction is halted by filtration through Whatman GF/C™ filters pretreated for 3 h with 0.05% polyethyleneimine. The filters are rinsed twice, each time with 5 ml of buffer at 4° C., and the radioactivity retained on each filter is measured by liquid scintigraphy. The nonspecific binding in the presence of 1 μM α-bungarotoxin is determined; the nonspecific binding represents approximately 60% of the total binding recovered on the filter. The percentage of inhibition of the specific binding of [³H]α-bungarotoxin is determined for each concentration of studied compound and then the $IC_{50}$ value, the concentration of compound which inhibits 50% of the specific binding, is calculated.

The $IC_{50}$ values of the highest-affinity compounds of the invention are from 0.005 to 20 μM.

The above results show that the compounds of the invention are ligands for nicotinic receptors. Certain of them are selective for receptors containing $\alpha_7$ subunits and others are of mixed nature for receptors of $\alpha_4\beta_2$ and $\alpha_7$ type.

The results of the tests suggest the use of the compounds in the treatment or the prevention of disorders linked to dysfunction of the nicotinic receptors, in particular at the central nervous system level.

These disorders comprise detrimental cognitive changes, more specifically detrimental memory changes, and also detrimental attentional changes, linked to Alzheimer's disease, to pathological ageing (age-associated memory impairment, AAMI), to Parkinsonian syndrome, to trisomy 21 (Down's syndrome), to Korsakoff's alcoholic syndrome or to vascular dementias (multi-infarct dementia, MDI).

The compounds of the invention could also be useful in the treatment of motor disorders observed in Parkinson's disease or of other neurological diseases, such as Huntington's chorea, Tourette's syndrome, tardive dyskinesia and hyperkinesia.

The compounds of the invention may also constitute a curative or symptomatic treatment for acute neurodegenerative pathologies, such as strokes and cerebral hypoxic episodes, and chronic neurodegenerative pathologies, such as Alzheimer's disease and Parkinson's disease. They may be used in cases of psychiatric pathology: schizophrenia, depression, anxiety, panic attacks, or compulsive or obsessional behavior.

They can prevent symptoms due to withdrawal from tobacco or alcohol, or various addictive substances, such as cocaine, LSD, cannabis, benzodiazepines.

The present invention therefore also provides pharmaceutical compositions comprising an effective dose of at least one compound of the invention, in the form of base or of salt or of pharmaceutically acceptable solvate, or in a mixture, where appropriate with suitable excipients.

The choice of the said excipients depends on the desired mode of administration and the pharmaceutical format.

The pharmaceutical compositions of the invention may therefore be intended for oral, sublingual, subcutaneous, intramuscular, intravenous, topical, intratracheal, intranasal, transdermic, rectal, or intraocular administration.

Examples of possible unitary administration forms are tablets, gelatin capsules, granules, powders, solutions or suspensions to be taken orally or to be injected, transdermal patches or suppositories. Ointments, lotions and collyria can be envisaged for topical administration.

The said unitary forms are dosed to permit daily administration of from 0.01 to 20 mg of active principle per kg of body weight, depending on the pharmaceutical dosage form.

To prepare tablets, the following materials are added to the active principle, micronized or non-micronized: a pharmaceutical vehicle, which can be composed of diluents, such as lactose, starch, or microcrystalline cellulose, or formulation adjuvants, such as binders (polyvinylpyrrolidone, hydroxypropylmethylcellulose, and the like), flow agents, such as silica, lubricants, such as magnesium stearate, stearic acid, glycerol tribehenate, sodium stearylfumarate. Wetting or surface-active agents, such as sodium lauryl sulfate, can also be added.

Possible preparation techniques are direct tableting, dry granulation, wet granulation or hot melt.

The tablets can be uncoated, sugar-coated, for example with sucrose, or coated with various polymers or other appropriate materials. They can be designed to permit rapid, delayed or sustained release of the active principle by virtue of polymer matrices or of specific polymers used in the coating.

To prepare gelatin capsules, the active principle is mixed with dry pharmaceutical vehicles (simple mixing, dry or wet granulation, or hot melt), or liquid or semisolid pharmaceutical vehicles.

The gelatin capsules can be hard or soft and may have a thin film coating, so as to have rapid, sustained or delayed activity (for example, for an enteric form).

A composition in the form of a syrup or an elixir or for administration in the form of drops can comprise the active principle in conjunction with a sweetener, preferably a calorie-free sweetener, methylparaben or propylparaben, as antiseptic, a flavor enhancer and a colorant.

The water-dispersible granules and powders may comprise the active principle in a mixture with the dispersing or wetting agents, or dispersing agents such as polyvinylpyrrolidone, and also with sweeteners and flavor-improvers.

For rectal administration, use is made of suppositories prepared with binders which melt at rectal temperature, for example cocoa butter or polyethylene glycols.

For parenteral administration, use is made of aqueous suspensions, isotonic saline solutions or injectable sterile solutions comprising pharmacologically compatible dispersing agents and/or wetting agents, for example propylene glycol or butylene glycol.

The active principle can also be formulated in the form of microcapsules, optionally with one or more vehicles or additives or else with a polymer matrix or with a cyclodextrin (transdermal patches or sustained release forms).

The topical compositions of the invention comprise a medium compatible with the skin. They can be provided in particular in the form of aqueous, alcoholic or aqueous/alcoholic solutions, of gels, of water-in-oil or oil-in-water emulsions having the appearance of a cream or of a gel, of microemulsions or of aerosols, or in the form of vesicular dispersions comprising ionic and/or nonionic lipids. These pharmaceutical dosage forms are prepared by methods conventional in the relevant fields.

Finally, the pharmaceutical compositions of the invention may comprise, in addition to a compound of general formula (I), other active principles which can be of use in the treatment of the disorders and diseases indicated above.

What is claimed is:

1. A compound selected from the group consisting of:
   5-[2-(2,4-dimethoxy-5-pyrimidinyl)-pyridin-5-yl]-1-azabicyclo[3.2.1]oct-2-ene hydrobromide (2:1);
   5-[2-(3,4-dimethoxyphenyl)pyridin-5-yl]-1-azabicyclo[3.2.1]oct-3-ene hydrobromide (2:1);
   5-[2-(3,4-dimethoxyphenyl)pyridin-5-yl]-1-azabicyclo[3.2.1]octane hydrobromide (2:1);
   5-[2-(2-fluorophenyl)pyridin-5-yl]-1-azabicyclo[3.2.1]oct-3-ene ethanedioate (1:1);
   5-[2-(3-methylphenyl)pyridin-5-yl]-1-azabicyclo[3.2.1]oct-3-ene ethanedioate (1:1);
   5-[2-(3-fluorophenyl)pyridin-5-yl]-1-azabicyclo[3.2.1]oct-3-ene ethanedioate (1:1);
   5-[2-(3-nitrophenyl)pyridin-5-yl]-1-azabicyclo[3.2.1]oct-3-ene ethanedioate (1:1);
   5-[2-(3-trifluoromethylphenyl)pyridin-5-yl]-1-azabicyclo[3.2.1]oct-3-ene ethanedioate (1:1);
   5-[2-(4-methylphenyl)pyridin-5-yl]-1-azabicyclo[3.2.1]oct-3-ene ethanedioate (1:1);
   5-[2-(3-thienyl)pyridin-5-yl]-1-azabicyclo[3.2.1]oct-3-ene ethanedioate (1:1);
   5-[2-(1,3-benzodioxol-5-yl)pyridin-5-yl]-1-azabicyclo[3.2.1]oct-3-ene ethanedioate (1:1);
   5-[2-(4-chlorophenyl)pyridin-5-yl]-1-azabicyclo[3.2.1]oct-3-ene ethanedioate (1:1);
   1-{3-[5-(1-azabicyclo[3.2.1]oct-3-en-5-yl)pyridin-2-yl]phenyl}ethanone ethanedioate (1:1);
   5-[2-(3-pyridinyl)pyridin-5-yl]-1-azabicyclo[3.2.1]oct-3-ene ethanedioate (1:1);
   5-[2-(5-indolyl)pyridin-5-yl]-1-azabicyclo[3.2.1]oct-3-ene ethanedioate (1:1);
   5-[2-(4-methoxyphenyl)pyridin-5-yl]-1-azabicyclo[3.2.1]oct-3-ene ethanedioate (1:1);
   5-[2-(3,5-dimethylphenyl)pyridin-5-yl]-1-azabicyclo[3.2.1]oct-3-ene ethanedioate (1:1);
   5-[2-(4-pyridinyl)pyridin-5-yl]-1-azabicyclo[3.2.1]oct-3-ene ethanedioate (1:1);
   5-[2-(4-methoxyphenyl)pyridin-5-yl]-1-azabicyclo[3.2.1]octane hydrobromide (2:1);

5-[2-(4-methylphenyl)pyridin-5-yl]-1-azabicyclo[3.2.1] octane hydrobromide (2:1);
5-[2-(3-methylphenyl)pyridin-5-yl]-1-azabicyclo[3.2.1] octane hydrobromide (2:1);
5-[2-(3,5-dimethylphenyl)pyridin-5-yl]-1-azabicyclo [3.2.1]octane hydrobromide (2:1);
5-[2-(3-fluorophenyl)pyridin-5-yl]-1-azabicyclo[3.2.1] octane hydrobromide (2:1);
5-[2-(3-thienyl)pyridin-5-yl]-1-azabicyclo[3.2.1]octane hydrobromide (2:1);
5-[2-(1,3-benzodioxol-5-yl)pyridin-5-yl]-1-azabicyclo [3.2.1]octane hydrobromide (2:1);
5-[2-(2-fluorophenyl)pyridin-5-yl]-1-azabicyclo[3.2.1] octane hydrobromide (2:1);
5-[2-(3-pyridinyl)pyridin-5-yl]-1-azabicyclo[3.2.1]octane hydrobromide (2:1);
5-[2-(4-pyridinyl)pyridin-5-yl]-1-azabicyclo[3.2.1]octane hydrobromide (2:1);
5-[2-(3-nitrophenyl)pyridin-5-yl]-1-azabicyclo[3.2.1]octane hydrobromide (2:1);
5-[2-(3-trifluorophenyl)pyridin-5-yl]-1-azabicyclo[3.2.1] octane hydrobromide (2:1);
5-[2-bromopyridin-5-yl]-1-azabicyclo[3.2.1]oct-3-ene hydrobromide (2:1);
5-[2-bromopyridin-5-yl]-1-azabicyclo[3.2.1]oct-2-ene hydrobromide (2:1);
5-[2-(4-piperidinyl)pyridin-5-yl]-1-azabicyclo[3.2.1]octane hydrobromide (2:1);
5-[2-(3-piperidinyl)pyridin-5-yl]-1-azabicyclo[3.2.1]octane hydrobromide (2:1);
(+)-5-[2-(4-methoxyphenyl)pyridin-5-yl]-1-azabicyclo [3.2.1]octane;
(−)-5-[2-(4-methoxyphenyl)pyridin-5-yl]-1-azabicyclo [3.2.1]octane;
(+)-5-[2-(3-fluorophenyl)pyridin-5-yl]-1-azabicyclo [3.2.1]octane;
(−)-5-[2-(3-fluorophenyl)pyridin-5-yl]-1-azabicyclo [3.2.1]octane;
5-[2-(2-thienyl)pyridin-5-yl]-1-azabicyclo[3.2.1]octane hydrobromide (2:1);
5-[2-(2-thienyl)pyridin-5-yl]-1-azabicyclo[3.2.1]oct-3-ene hydrobromide (2:1);
5-[2-(5-methyl-2-thienyl)pyridin-5-yl]-1-azabicyclo [3.2.1]oct-3-ene hydrobromide (2:1);
5-[2-(5-methyl-2-thienyl)pyridin-5-yl]-1-azabicyclo [3.2.1]octane hydrobromide (2:1);
5-[2-(5-chloro-2-thienyl)pyridin-5-yl]-1-azabicyclo [3.2.1]octane hydrobromide (2:1);
5-[2-(5-chloro-2-thienyl)pyridin-5-yl]-1-azabicyclo [3.2.1]oct-3-ene hydrobromide (2:1);
5-[2-(2-furyl)pyridin-5-yl]-1-azabicyclo[3.2.1]oct-3-ene hydrobromide (2:1);
5-[2-(2-furyl)pyridin-5-yl]-1-azabicyclo[3.2.1]octane hydrobromide (2:1);
5-[2-(5-indolyl)pyridin-5-yl]-1-azabicyclo[3.2.1]octane ethanedioate (1:1);
5-[2-(2-benzofuryl)pyridin-5-yl]-1-azabicyclo[3.2.1]oct-3-ene;
5-[2-(2-benzofuryl)pyridin-5-yl]-1-azabicyclo[3.2.1]octane hydrobromide (2:1);
5-[2-(2-pyrrolyl)pyridin-5-yl]-1-azabicyclo[3.2.1]oct-3-ene hydrobromide (2:1);
5-[2-(2-pyrrolyl)pyridin-5-yl]-1-azabicyclo[3.2.1]octane ethanedioate (1:1);
5-[2-(2-benzothienyl)pyridin-5-yl]-1-azabicyclo[3.2.1] oct-3-ene;
5-[2-(2-benzothienyl)pyridin-5-yl]-1-azabicyclo[3.2.1] octane hydrobromide (2:1);
5-[2-(3-furyl)pyridin-5-yl]-1-azabicyclo[3.2.1]oct-3-ene hydrobromide (2:1);
5-[2-(3-furyl)pyridin-5-yl]-1-azabicyclo[3.2.1]octane hydrobromide (2:1);
5-[2-(4-hydroxy-3-pyridinyl)pyridin-5-yl]-1-azabicyclo [3.2.1]octane hydrobromide (2:1);
5-[2-(3,5-dimethyl-1,2-oxazol-4-yl)pyridin-5-yl]-1-azabicyclo[3.2.1]octane;
5-[2-(3,5-dimethyl-1,2-oxazol-4-yl)pyridin-5-yl]-1-azabicyclo[3.2.1]oct-3-ene hydrobromide (2:1);
5-[2-(2,4-dimethoxypyrimidin-5-yl)pyridin-5-yl]-1-azabicyclo[3.2.1]octane ethanedioate (1:1);
5-[2-(4-methyl-2-thienyl)pyridin-5-yl]-1-azabicyclo [3.2.1]octane hydrobromide (2:1);
5-[2-(4-methyl-2-thienyl)pyridin-5-yl]-1-azabicyclo [3.2.1]oct-3-ene hydrobromide (2:1);
5-[2-(1-dibenzofuryl)pyridin-5-yl]-1-azabicyclo[3.2.1] octane hydrobromide (2:1);
5-[2-(1-dibenzofuryl)pyridin-5-yl]-1-azabicyclo[3.2.1] oct-3-ene hydrobromide (2:1);
5-[2-(1-phenoxatiinyl)pyridin-5-yl]-1-azabicyclo[3.2.1] oct-3-ene hydrobromide (2:1);
5-[2-(1-phenoxatiinyl)pyridin-5-yl]-1-azabicyclo[3.2.1] octane hydrobromide (2:1);
5-[2-(8-quinoleinyl)pyridin-5-yl]-1-azabicyclo[3.2.1]octane hydrobromide (2:1);
5-[2-(8-quinoleinyl)pyridin-5-yl]-1-azabicyclo[3.2.1]oct-3-ene hydrobromide (2:1);
5-[2-(3-benzothienyl)pyridin-5-yl]-1-azabicyclo[3.2.1] oct-3-ene hydrobromide (2:1);
5-[2-(3-benzothienyl)pyridin-5-yl]-1-azabicyclo[3.2.1] octane ethanedioate (1:1).

2. A compound selected from the group consisting of:
5-(2-phenylpyridin-5-yl)-1-azabicyclo[3.2.1]oct-3-ene hydrobromide (2:1);
5-(2-phenylpyridin-5-yl)-1-azabicyclo[3.2.1]octane hydrobromide (2:1);
5-(2-phenylpyridin-5-yl)-1-azabicyclo[3.2.1]oct-2-ene hydrobromide (2:1).

* * * * *